United States Patent [19]

Rule

[11] Patent Number: 4,885,423

[45] Date of Patent: Dec. 5, 1989

[54] PROCESS FOR PREPARATION OF AROMATIC DIMERS

[75] Inventor: Mark Rule, Kingsport, Tenn.

[73] Assignee: Eastman Kodak Company, Rochester, N.Y.

[21] Appl. No.: 350,667

[22] Filed: May 11, 1989

Related U.S. Application Data

[63] Continuation-in-part of Ser. No. 198,360, May 25, 1988, abandoned.

[51] Int. Cl.$^4$ .................................................. C07C 2/00
[52] U.S. Cl. ........................................ 585/427; 585/425
[58] Field of Search ................ 585/425, 427; 570/204, 570/182

[56] References Cited

U.S. PATENT DOCUMENTS

| | | | |
|---|---|---|---|
| 2,907,799 | 10/1959 | Hughes et al. | 585/427 |
| 3,578,716 | 5/1971 | Robinson et al. | 585/425 |
| 4,022,795 | 5/1977 | Bamfield et al. | 585/427 |
| 4,720,576 | 1/1988 | Wada et al. | 585/427 |

FOREIGN PATENT DOCUMENTS

| | | | |
|---|---|---|---|
| 6307372 | 5/1987 | European Pat. Off. | 585/427 |
| 4040467 | 12/1970 | Japan | 585/425 |

OTHER PUBLICATIONS

Sanisbury, Tetrahedron, 36, 3327 (1980).

*Primary Examiner*—Asok Pal
*Attorney, Agent, or Firm*—Charles R. Martin; William P. Heath, Jr.

[57] ABSTRACT

A process for preparation of an aromatic dimer compound corresponding to the structure $$I_xAr-ArI_x$$

wherein x is 0, 1, 2, 3, 4, or 5 and Ar is a divalent aromatic radical containing 6 to 14 carbon atoms comprising contacting, at a sufficient temperature and pressure in the absence of carbon monoxide and in the absence of an alkali metal compound or an alkaline earth metal compound, platinum and an aromatic iodide compound corresponding to the structure $$Ar-I_x$$

where Ar is a monovalent aromatic radical and x is 1, 2, 3, 4, 5, or 6.

7 Claims, No Drawings

PROCESS FOR PREPARATION OF AROMATIC DIMERS

This application is a continuation-in-part of Ser. No. 198,360 filed May 25, 1988.

This invention relates to a process for preparation of an aromatic dimer by coupling two iodine substituted aromatic molecules in the presence of platinum.

Processes to form a carbon-carbon bond between two aryl halides are well known in the art. Thus, the Ullmann coupling reaction utilizes a stoichiometric amount of copper to form biaryls. It is also known that stoichiometric amounts of nickel tetrakis(triphenylphosphine) in dimethyl formamide will cause the coupling of aryl iodides. Nickel salts will catalyzed the coupling of aryl iodides if a stoichiometric amount of a reducing agent is present, such as zinc metal or hydrazine. Palladium will catalyze the coupling of aryl halides in the presence of a reducing agent, such as hydrazine, zinc metal, or magnesium metal. These and other methods are reviewed by M. Sainsbury (Tetrahedron No. 36, 3327, 1989). More recently, EP No. 86307372.2 describes the coupling of aromatic halides in the presence of a platinum group metal, specifically palladium and rhodium, carbon monoxide and stoichiometric amounts of alkali or alkaline earth bases. The purpose of the base is to accept the released halide.

A deficiency in all of these processes is that they require the utilization of a stoichiometric amount of reactant to combine with the released halide. This increases the cost of the process and the halide values are difficult to recover from the halide compound. Another deficiency of these processes is they all produce unwanted by-products to varying degrees. Therefore a coupling process from which the halide values could readily be recovered and which did not require the use of a stoichiometric reducing agent or produce undesired by-products would be an advancement in the state of art.

Accordingly, one object of the present invention is to provide a process for coupling aryl iodides which does not require a stoichiometric amount of a reducing agent. Another object of the present invention is to provide a process for coupling aryl iodides where the iodide values can be recovered directly in the form of elemental iodine and which does not produce undesired by-products.

Broadly, I have now discovered that platinum catalytically couples aromatic iodides. The overall reaction is $$2\ ArI \rightarrow Ar\text{-}Ar + I_2$$

In an optional embodiment the aromatic iodide can be further substituted with up to five iodine atoms in addition to the one iodine atom required for coupling. In this embodiment the aromatic iodide compound corresponds to the structure $$Ar\text{-}I_x$$

where Ar is a monovalent aromatic radical and x is 1, 2, 3, 4, 5, or 6.

In this embodiment the process can be thought of as a process for preparation of an aromatic dimer compound corresponding to the structure $$I_xAr\text{-}ArI_x$$

wherein x is 0, 1, 2, 3, 4, or 5, and Ar is a divalent aromatic radical containing 6 to 14 carbon atoms comprising contacting, at a sufficient temperature and pressure, platinum and an aromatic iodide compound corresponding to the structure $$Ar\text{-}I_x$$

where Ar is a monovalent aromatic radical and x is a 1, 2, 3, 4, 5, or 6.

When x equals one, coupling to form the corresponding dimer occurs and can be carried to complete reaction. When x equal two, coupling yields the corresponding diiodoinated dimer at low conversions and oligomeric or polymeric product at high conversion. When x equals three high conversions yield branched or cross-linked polymer. Since undesired side reactions, such as carbonylation or reduction to the parent hydrocarbon are essentially absent in the process of the present invention, the product yield can be taken to high levels with proper selection of reaction conditions.

The aromatic iodide compounds useful in this invention can vary widely and can be selected from the group consisting of iodine substituted hydrocarbon aromatics, iodine substituted sulfur containing aromatics, iodine substituted nitrogen containing aromatics, and iodine substituted oxygen containing aromatics. Examples of suitable hydrocarbon aromatics are benzene, biphenyl, naphthalene, and anthracene substituted with iodine. Examples of suitable sulfur-containing aromatics are diphenyl sulfone, diphenyl sulfide, and diphenyl sulfoxide substituted with iodine. Examples of suitable nitrogen-containing aromatics are pyridine, and quinoline substituted with iodine. Preferably an iodine substituted hydrocarbon aromatic is used and the hydrocarbon aromatic is preferably selected from the group consisting of benzene, naphthalene, and biphenyl. Other substituents on the aromatic ring are also possible and can include methyl, ethyl, or other alkyl, oxyalkyl, carboxylic acid and esters, nitrile, halogens such as fluoro, chloro, bromo or iodo, and nitro substituents.

The form of the platinum utilized is not critical. The platinum can be added to the reaction as platinum oxide, platinum bromide, platinum chloride, chloroplatinic acid, platinum on carbon, platinum on alumina, or as platinum black. The amount utilized is not critical, but the reaction rate increases with increasing amounts of platinum. The amount utilized can be between 0.001 and 10 mol %, preferably between 0.01 and 1 mol %, based on the amount of aryl iodide reacted. Other platinum group metals, such as rhodium, palladium, and iridium are not effective as catalysts under the conditions of the present invention.

The reaction can be run either in liquid or vapor phase. When run in the vapor phase, it is convenient to support the platinum on an inert support such as alumina or carbon and pass the aryl iodide across the catalyst. The same apparatus can be utilized in a trickle-bed fashion. Alternatively, the catalyst can be suspended in a melt or solution of the reactant and the reaction will proceed in the liquid phase. The reaction pressure is not critical, and subatmospheric to superatmospheric pressures are suitable. For vapor phase operation, near atmospheric pressure is preferred; while for liquid phase, sub- or superatmospheric pressure will be desired, depending on the normal boiling point of the reactant and the desire to strip iodine out of the reaction mixture. When run in the liquid phase, the reactant can be either neat or with an inert cosolvent. Suitable cosolvents include high boiling aromatic hydrocarbons, such as terphenyl, diphenyl ether, diphenyl sulfone, and the like. When run in the vapor phase, the reactant can be either neat or diluted with an inert gas or vapor. Inert gases includes argon and nitrogen. Inert vapors include benzene, hexane, and methane.

The reaction temperature is not critical. Temperatures above 250° C. are preferred. Below about 250° the reaction rate becomes slow. Above 350° C. degradation reactions of the aryl iodides or their reaction products become unacceptable. The most preferred temperatures are in the range of 275° to 350° C.

Reaction time is not critical. Typical reaction times will depend on the reaction temperature, but in general vary between 2 and 24 hours for liquid phase reactions. For vapor phase reactions, the residence time can vary between 0.1 and 40 seconds, preferably between 0.2 and 10 seconds.

Recovery of the platinum depends on the process and product, but in general the platinum can be recovered by filtration of the reaction product. The recovered platinum is suitable for reuse without further treatment.

The process of this invention is conducted in the absence of carbon monoxide. This is an important aspect of this invention because the absence of carbon monoxide results in higher yields and fewer reaction byproducts, such as. carbonyated or hydrogenated aromatics.

The process of this invention is conducted in the absence of an alkali metal compound or an alkaline earth metal compound. This is as important aspect of this invention because the existence of an alkali metal compound or an alkaline earth metal compound significantly complicates recovery of the iodine because the iodine combines with these compounds to form salts that are difficult to recover and even when the salts are recovered it is difficult to recover the iodine from the salts.

The following examples illustrate the practice of this invention.

EXAMPLE 1

100 grams of p-diiodobenzene was heated to 285° C. The molten diiodobenzene was a light straw color. After 2 hours the melt appeared unchanged, and gas chromatography analysis of an aliquot showed 100% p-diiodobenzene. On addition of 0.1 grams of platinum bromide, iodine evolution began. After 4 hours, gas chromatography analysis of an aliquot showed the presence of 15 mol % 4,4'-diiodobiphenyl. No other diiodobiphenyl isomers were detected, nor was any iodobiphenyl or biphenyl.

EXAMPLE 2

The following catalysts were tested for activity in the reaction of the present invention by placing the specified amount of catalyst in 10 grams of p-diiodobenzene and heating in a test tube at 275° C. The catalyst was judged to be active if iodine was observed to evolve from the reaction mixture within 2 hours.

| Catalyst | Amount (g) | Catalyst Active? |
|---|---|---|
| RhCl3 | 0.05 | No |
| PdCl2 | 0.05 | No |
| Pd(OAc)2 | 0.05 | No |
| RuCl3 | 0.05 | No |
| Re powder | 0.03 | No |
| Ni powder | 0.10 | No |
| IrCl3 | 0.05 | No |
| AuCl3 | 0.05 | No |
| PtO2 | 0.05 | Yes |
| 5% Pt/Al2O3 | 0.50 | Yes |
| 1% Pt/C | 0.30 | Yes |
| PtBr2 | 0.03 | Yes |

EXAMPLE 3

100 grams of 2,6 diiodonaphthalene and 0.1 grams of PtO2 were placed in a 500-mL, round-bottom flask fitted with a metal stirrer and attached to a 200-torr vacuum source. On heating to 275° C. iodine evolved over 3 hours, then the temperature was gradually raised to 350° C. The reaction melt gradually became solid. After 12 hours the reaction was stopped and the product analyzed. Found: C=77.21%, H-3.44%, I (by difference)=19.35%, which corresponds to an average degree of polymerization to polynaphthalene of 8.5 and a degree of conversion of 88%.

EXAMPLE 4

A 1-inch diameter quartz tube containing 25 mL of 1.24% Pt/C pellets (6-8 mesh) was heated to 400° C. under nitrogen flow (250 mL/minute). Iodobenzene was added dropwise at 0.034 mL/minute. After three hours, analysis of the reaction product by GC showed a conversion to biphenyl of 1.0 mole %.

Obviously, numerous modifications and variations of the present invention are possible in light of the above teachings. It is therefore to be understood that within the scope of the appended claims, the invention may be practiced otherwise than as specifically described herein.

I claim:

1. A process comprising preparation of iodine and an aromatic dimer compound corresponding to the structure IxAr-ArIx wherein x is 0, 1, 2, 3, 4, or 5, and Ar is a divalent aromatic radical containing 6 to 14 carbon atoms comprising contacting platinum and an aromatic iodide compound corresponding to the structure Ar-Ix where Ar is a aromatic radical and x is 1, 2, 3, 4, 5, or 6. the contacting being at a sufficient temperature and a sufficient pressure and in the absence of carbon monoxide and in the absence of an alkali metal compound and in the absence of an alkaline earth metal compound.

2. The process of claim 1 wherein the temperature is above 250° C.

3. The process of claim 1 wherein the temperature is in the range of 275° to 350° C.

4. The process of claim 1 wherein Ar is a hydrocarbon aromatic selected from the group consisting of iodobenzene, diiodobenzene, and diiodonaphthalene.

5. The process of claim 1 wherein the aromatic iodide compound is contacted with platinum in the gas phase.

6. The process of claim 1 wherein the aromatic iodide compound is contacted with platinum in the presence of an inert solvent.

7. The process of claim 1 wherein the aromatic iodide compound corresponds to the structure Ar-Ix where x is 1.

* * * * *